United States Patent [19]

Bergmeier et al.

[11] Patent Number: 4,996,201

[45] Date of Patent: Feb. 26, 1991

[54] 4-(N-SUBSTITUTED AMINO)-2-BUTYNYL-1-CARBAMATES AND THIOCARBAMATES AND DERIVATIVES THEREOF AS CENTRALLY ACTING MUSCARINIC AGENTS

[75] Inventors: Stephen C. Bergmeier; Jeffrey A. Kester; Walter H. Moos; Haile Tecle; Anthony J. Thomas, all of Ann Arbor, Mich.

[73] Assignee: Warner-Lambert Co., Morris Plains, N.J.

[21] Appl. No.: 388,777

[22] Filed: Aug. 2, 1989

[51] Int. Cl.$^5$ ................ A61K 31/395; C07D 223/04
[52] U.S. Cl. ................................ 514/212; 540/450; 540/609; 544/162; 544/400; 546/233; 546/242; 548/567; 548/569; 548/950; 548/967; 558/232; 560/27; 560/29; 560/30; 560/31; 560/32; 560/33; 560/159; 514/315; 514/331; 514/428; 514/478; 514/237.8; 514/255; 514/484; 514/487; 514/488; 514/489; 514/490
[58] Field of Search ............. 548/567, 569, 967, 950; 514/428, 315, 478, 237.8, 255, 183, 210, 331, 212, 484, 486, 487, 488, 489, 490; 560/159, 27, 29, 30, 31, 32, 33; 546/247, 233; 544/162, 400; 558/232; 540/450, 609

[56] References Cited

U.S. PATENT DOCUMENTS

| | | | |
|---|---|---|---|
| 3,131,213 | 4/1964 | Suney et al. | 544/400 |
| 3,354,178 | 11/1967 | Dickinson | 546/247 |
| 3,452,031 | 6/1969 | Parcell | 546/247 |
| 4,065,471 | 12/1977 | Dickinson | 546/247 |

OTHER PUBLICATIONS

*Chemical Abstracts* 106: 137654E "Synthesis of vicinal Amino Carbamate of acetylenes," (1987).
M. V. Mavrov, et al., Izvestiya Akademii Nauk SSR, Seriya Khimicheskaya, vol. 7, pp. 1568–1571 (196), Eng. trans.
Journal of Medicinal Chemistry, 10:615 (1967) Neumeyer, et al, Pharmacologically Active Acetylene Compounds, I. Structural Modifications of Oxotremorine.
Brit. J. Pharmacol. (1966), 26,56–67 A30 A. Bebbington, et al The Central and Peripheral Activity of Acetylenic Amines Related to Oxotremorine.

*Primary Examiner*—Richard L. Raymond
*Assistant Examiner*—Mark W. Russell
*Attorney, Agent, or Firm*—Francis J. Tinney

[57] ABSTRACT

4-(N-Substituted amino)-2-butynyl-1-carbamates and thiocarbamates and derivatives thereof are described, as well as methods for the preparation and pharmaceutical compositions of same, which are useful as centrally acting muscarinic agents and are useful as analgesic agents for the treatment of pain, as sleep aids and as agents for treating the symptoms of senile dementia, Alzheimer's disease, Huntington's chorea, tardive dyskinesia, hyperkinesia, mania, or similar conditions of cerebral insufficiency characterized by decreased cerebral acetylcholine production or release.

6 Claims, No Drawings

4-(N-SUBSTITUTED AMINO)-2-BUTYNYL-1-CARBAMATES AND THIOCARBAMATES AND DERIVATIVES THEREOF AS CENTRALLY ACTING MUSCARINIC AGENTS

BACKGROUND OF THE INVENTION

The present invention relates to novel 4-(N-substituted amino)-2-butynyl-1-carbamates and thiocarbamates and derivatives thereof useful as pharmaceutical agents, to methods for their production, to pharmaceutical compositions which include these compounds and a pharmaceutically acceptable carrier, and to pharmaceutical methods of treatment. More particularly, the novel compounds of the present invention are centrally acting muscarinic agents useful in treating the symptoms of cognitive decline in an elderly patient.

Disorders of cognition are generally characterized by symptoms of forgetfulness, confusion, memory loss, attentional deficits and/or, in some cases, affective disturbances. These symptoms may arise as a result of the general aging process and/or from organic brain disease, cerebrovascular disease, head injury or developmental or genetic defects.

The general decrease in cognitive function which accompanies the aging process is well accepted. The same phenomenon has been observed and documented in many lower mammals, including those routinely employed in pharmacological testing programs for screening and predicting usefulness for particular drugs in higher animals, including humans.

Although disorders of cognition often accompany the general aging process, presenile and senile primary degenerative dementia are the most common accepted causes of mental deterioration in the elderly. It has been estimated that at least ten percent of persons overt sixty years of age will eventually suffer severe mental deterioration. A much larger number will experience cognitive decline of sufficient severity to impede their activities.

Many of the symptoms of cognitive disorders, especially impaired memory, are associated with decreased acetylcholine synthesis and the impairment of cholinoreceptive neurons. In the hippocampus and cerebral cortex of patients suffering from primary degenerative dementia for example, the level of the enzyme choline acetyltransferase (CAT) can be reduced as much as ninety percent (see Davies, P., et al, The Lancet, 2, page 1403 (1976); Perry, E. K., et al, Journal of Neurological Sciences, 34, pages 247 to 265 (1977); and White, P., et al, The Lancet, 1, pages 668 to 670 (1977)).

Since CAT catalyzes the synthesis of acetylcholine from its precursors choline and acetyl coenzyme A, the loss of CAT reflects the loss of cholinergic or acetylcholine-releasing nerve endings in the hippocampus and cerebral cortex. There is abundant evidence that cholinergic terminals in the hippocampus are critically important for memory formation.

The cholinergic hypothesis suggests that drugs which restore acetylcholine levels or cholinergic function (i.e., cholinomimetic) are effective in correcting this deficit in neurotransmitter chemical and provide treatment of the memory impairment symptom of cerebral insufficiency. Considerable biochemical, pharmacological, and electrophysiological evidence supports the hypothesis that deficits in the cholinergic system underlie geriatric cognitive dysfunction (Peterson, C. and Gibson, B. E., Neurobiology of Aging, 4, pages 25 to 30 (1983)). Aged humans and nonhuman primates with decreased cognition show improved memory when they are treated, for example, with acetylcholinesterase inhibitors such as physostigmine. These agents increase the available supply of synaptic acetylcholine by inhibiting its hydrolysis.

Aminopyridines such as 3,4-diaminopyridine ameliorate age-related cognitive deficits by increasing the release of acetylcholine from presynaptic nerve terminals, thus increasing synaptic acetylcholine (see Davis, H. P., et al, Experimental Aging Research, 9, pages 211 to 214 (1983)).

It has been known for some time that the natural alkaloid, muscarine, has the ability to act relatively selectively at autonomic effector cells to produce qualitatively the same effect as acetylcholine. Two other agents, pilocarpine and oxotremorine, have the same principal sites of action as muscarine and acetylcholine and are thus classified as having "muscarinic" action. Although these agents are of great value as pharmacological tools, present clinical use is largely restricted to the use of pilocarpine as a miotic agent.

Oxotremorine (1-pyrrolidino-4-(2-oxopyrrolidino)-2-butyne) was discovered while exploring the pharmacologic actions of tremorine. During the course of screening drugs in mice, it was observed that tremorine (1,4-dipyrrolidino-2-butyne) produced a profound tremor of the head and limbs lasting for more than one hour (see Everett, G. M., Science, 124, page 79 (1956)). It was later discovered that tremorine is converted to an active metabolite, oxotremorine, which is responsible for its pharmacological properties.

A series of N-(4-amino-2-butynyl)-N-alkylcarboxamides useful as central nervous system stimulants is disclosed in U.S. Pat. No. 3,354,178.

A series of N-(4-amino-2-butynyl)imides useful as central nervous system stimulants and depressants is disclosed in U.S. Pat. No. 4,065,471.

Further, derivatives containing a 2-oxazolidinone group are disclosed in U.S. Pat. Nos. 3,354,178 and 4,065,471.

The central and peripheral activity of a series of acetylenic amines related to oxotremorine is disclosed by Bebbington, A., et al, British Journal of Pharmacology 26, pages 56 to 67 (1966). The pharmacological properties of additional structural modifications of oxotremorine are disclosed by Neumeyer, J. L., et al, Journal of Medicinal Chemistry 10, pages 615 to 620 (1967).

However, none of the compounds disclosed in the aforementioned references suggests the combination of structural variations of the compounds of the present invention described hereinafter. Furthermore, the aforementioned compounds are not disclosed for treating the symptoms of cognitive decline in an elderly patient.

SUMMARY OF THE INVENTION

Accordingly, the present invention is a compound of Formula I

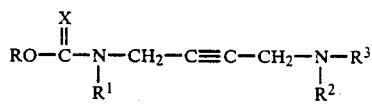

wherein R is alkyl of from one to six carbon atoms,
alkyl of from one to six carbon atoms substituted with hydroxy or alkoxy of from one to four carbon atoms,
alkenyl of from two to six carbon atoms,
alkenyl of from two to six carbon atoms substituted with hydroxy or alkoxy of from one to four carbon atoms,
alkynyl of from two to six carbon atoms,
alkynyl of from two to six carbon atoms substituted with hydroxy or alkoxy of from one to four carbon atoms,
cycloalkyl of from three to six carbon atoms,

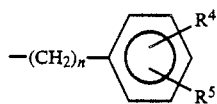

wherein n is zero or an integer of one to eight and $R^4$ and $R^5$ are independently hydrogen, fluorine, chlorine, bromine, hydroxy, alkyl of from one to three carbon atoms, or alkoxy of from one to four carbon atoms, or

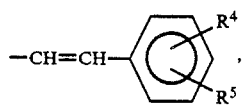

wherein
$R^4$ and $R^5$ are as defined above;
X is oxygen or sulfur;
$R^1$ is hydrogen,
  alkyl of from one to six carbon atoms,
  alkyl of from one to six carbon atoms substituted with hydroxy or alkoxy of from one to four carbon atoms,
  alkenyl of from three to six carbon atoms,
  alkenyl of from three to six carbon atoms substituted with hydroxy or alkoxy of from one to four carbon atoms,
  alkynyl of from three to six carbon atoms,
  alkynyl of from three to six carbon atoms substituted with hydroxy or alkoxy of from one to four carbon atoms,
  cycloalkyl of from three to six carbon atoms, or

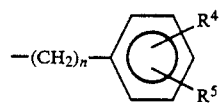

wherein n, $R^4$ and $R^5$ are as defined above;
$R^2$ and $R^5$ are each independently
  hydrogen,
  alkyl of from one to twenty carbon atoms,
  alkyl of from one to twenty carbon atoms substituted with hydroxy or alkoxy of from one to four carbon atoms,
  alkenyl of from three to twenty carbon atoms,
  alkenyl of from three to twenty carbon atoms substituted with hydroxy or alkoxy of from one to four carbon atoms,
  alkynyl of from three to twenty carbon atoms,
  alkynyl of from three to twenty carbon atoms substituted with hydroxy or alkoxy of from one to four carbon atoms,
  cycloalkyl of from three to eight carbon atoms,
  phenyl,
  phenyl substituted with alkyl of from one to four carbon atoms, alkyl of from one to four carbon atoms substituted with hydroxy or alkoxy of from one to four carbon atoms, alkoxy of from one to four carbon atoms, chlorine, bromine, hydroxy, nitro or trifluoromethyl or
$R^2$ and $R^3$ are taken together with the nitrogen atom to which they are attached to form a ring denoted by

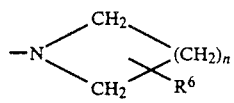

wherein $R^5$ is hydrogen, alkyl of from one to ten carbon atoms, alkyl of from one to ten carbon atoms substituted with hydroxy or alkoxy of from one to four carbon atoms, alkenyl of from two to ten carbon atoms, alkenyl of from two to ten carbon atoms substituted with hydroxy or alkoxy of from one to four carbon atoms, alkynyl of from two to ten carbon atoms or alkynyl of from two to ten carbon atoms substituted with hydroxy or alkoxy of from one to four carbon atoms and n is as defined above,

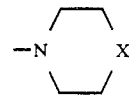

wherein X is as defined above or

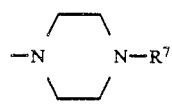

wherein $R^7$ is hydrogen or alkyl of from one to six carbon atoms, or
a pharmaceutically acceptable acid addition salt thereof.

As centrally acting muscarinic agents, the compounds of Formula I are useful as analgesic agents for the treatment of pain in mammals including man, as sleep aids, and as agents for treating the symptoms of senile dementia, Alzheimer's disease, Huntington's chorea, tardive dyskinesia, hyperkinesia, mania or similar conditions of cerebral insufficiency characterized by decreased cerebral acetylcholine production or release.

A still further embodiment of the present invention is a pharmaceutical composition for administering an effective amount of a compound of Formula I in unit dosage form in the treatment methods mentioned above.

Finally, the present invention is directed to methods for production of a compound of Formula I.

DETAILED DESCRIPTION OF THE INVENTION

In the compounds of Formula I, the term "alkyl" means a straight or branched hydrocarbon radical having from one to twenty carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl, undecyl, dodecyl, tridecyl, tetradecyl, pentadecyl, hexadecyl, heptadecyl, octadecyl, nonadecyl, eicodecyl, and the like.

The term "alkenyl" means a straight or branched unsaturated hydrocarbon radical having from two to twenty carbon atoms and includes, for example, ethenyl, 2-propenyl, 1-butenyl, 2-butenyl, 1-pentenyl, 2-pentenyl, 3-methyl-3-butenyl, 1-hexenyl, 2-hexenyl, 3-hexenyl, 3-heptenyl, 1-octenyl, 1-nonenyl, 1-decenyl, 1-undecenyl, 1-dodecenyl, 1-tridecenyl, 1-tetradecenyl, 1-pentadecenyl, 1-hexadecenyl, 1-heptadecenyl, 1-octadecenyl, 1-nonadecenyl, 1-eicodenyl, and the like.

The term "alkynyl" means a straight or branched triple bonded unsaturated hydrocarbon radical having from two to twenty carbon atoms and includes, for example, ethynyl, 2-propynyl, 1-butynyl, 2-butynyl, 3-butynyl, 1-pentynyl, 3-pentynyl, 1-hexynyl, 2-hexynyl, 3-hexynyl, 3-heptynyl, 1-octynyl, 2-octynyl, 1-nonynyl, 2-nonynyl, 3-nonynyl, 4-nonynyl, 1-decynyl, 2-decynyl, 2-undecynyl, 3-undecynyl, 3-dedecynyl, 3-tridecynyl, 1-tetradecynyl, 3-tetradecynyl, 3-pentadecynyl, 3-hexadecynyl, 1-heptadecynyl, 3-octadecynyl, 3-nonadecynyl, 3-eicodecynyl, and the like.

The term "alkoxy" means alkyl-O- of from one to four carbon atoms as defined above for "alkyl."

The term "cycloalkyl" means a saturated hydrocarbon ring having three to eight carbon atoms and includes, for example, cyclopropyl, cyclobutyl, cyclopentyl, cyclohexyl, cycloheptyl, cyclooctyl, and the like.

"Halogen" is fluorine, chlorine, bromine, or iodine.

Pharmaceutically acceptable acid addition salts of the compounds of Formula I include salts derived from nontoxic inorganic acids, such as hydrochloric, nitric, phosphoric, sulfuric, hydrobromic, hydriodic, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge, S. M., et al, "Pharmaceutical Salts," *Journal of Pharmaceutical Science*, Vol. 66, pages 1-19 (1977)).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free bases for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess asymmetric carbon atoms (optical centers); the racemates as well as the individual enantiomers are intended to be encompassed within the scope of the present invention.

A preferred compound of Formula I is one wherein R is
  alkyl of from one to six carbon atoms, or
  alkenyl of from two to six carbon atoms;
X is oxygen;
$R^1$ is hydrogen, or alkyl of from two to six carbon atoms;
$R^2$ and $R^3$ are each independently
  hydrogen,
  alkyl of from one to twenty carbon atoms,
  alkyl of from one to twenty carbon atoms substituted with hydroxy or alkoxy of from one to four carbon atoms,
  alkenyl of from three to twenty carbon atoms,
  alkynyl of from three to twenty carbon atoms or
  $R^2$ and $R^3$ are taken together with the nitrogen atom to which they are attached to form a ring denoted by

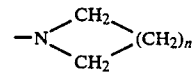

wherein n is zero or an integer from one to eight,

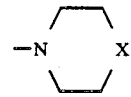

wherein X is oxygen or sulfur or

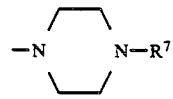

wherein $R^7$ is hydrogen or alkyl of from one to six carbon atoms.

A further embodiment is a compound of Formula I in which R is methyl, ethyl, or ethenyl;
X is oxygen;
$R^1$ is hydrogen, methyl, or ethyl,
$R^2$ and $R^3$ are each independently hydrogen, methyl, ethyl, $-(CH_2)_n-OH$, wherein n is an integer from three to four, $-CH_2C \equiv CH$ or $R^2$ and $R^3$ are taken together with the nitrogen atoms to which they are attached to form a ring denoted by

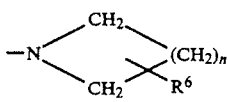

wherein n is zero or an integer from one to six,

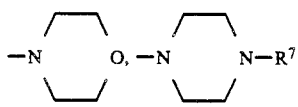

wherein R⁷ is hydrogen or methyl.

Particularly valuable are:

Methyl[methyl4-(1-pyrrolidinyl)-2-butynyl]]carbamate;
Methyl methyl4-(1-piperidinyl)-2-butynyl]carbamate;
Methyl[4-(hexahydro-1H-azepin-1-yl)-2-butynyl]-methyl-carbamate;
Methyl[4-(dimethylamino)-2-butynyl]methylcarbamate;
Methyl[4-(ethylmethylamino)-2-butynyl]methylcarbamate;
Methyl[4-(1-pyrrolidinyl)-2-butynyl]-carbamate;
Methyl ethyl[4-(1-pyrrolidinyl)-2-butynyl]carbamate;
Ethyl[4-(1-pyrrolidinyl)-2-butynyl-carbamate;
Ethyl methyl[4-(1-pyrrolidinyl)-2-butynyl]carbamate;
Ethenyl methyl[4-(1-pyrrolidinyl)-2-butynyl)]carbamate;
Methyl4-(1-azetidinyl)-2-butynyl]methylcarbamate;
Methyl methyl[4-(4-morpholinyl)-2-butynyl]carbamate;
Methyl methyl[4-(4-methyl-1-piperazinyl)-2-butynyl]-carbamate;
Methyl methyl[4-(methylamino)-2-butynyl]carbamate;
Methyl[4-(diethylamino)-2-butynyl]methylcarbamate;
Methyl methyl4-[methyl(2-propynyl)amino]-2-butynyl]-carbamate;
Methyl[4-[(3-hydroxypropyl)methylamino]-2-butynyl]methyl-carbamate; and
Methyl[4-[(4-hydroxybutyl)methylamino]-2-butynyl]methyl-carbamate; or a pharmaceutically acceptable acid addition salt thereof.

The compounds of Formula I are valuable centrally acting muscarinic agents. The biological activity of compounds of the present invention was evaluated using a number of tests. The activity of compounds of the present invention as central muscarinic binding site agonists and antagonists was measured. Thus, in the Receptor [³H]Quinuclidinyl Benzilate Binding Assay (RQNB), described more fully by Watson, M., et al, *Journal of Pharmacology and Experimental Therapeutics*, 237, pages 411 to 418 (1986), rat cerebral cortex tissue is treated with radiolabeled quinuclidinyl benzilate, a known muscarinic binding site antagonist. The concentration of test compound required to inhibit 50% of the binding of this muscarinic antagonist is then determined. This procedure allows a determination of the affinity of the test compounds for the central muscarinic antagonist site. Similarly in the Receptor [³H]Cis-methyldioxalane Assay (RCMD), described more fully by Vickroy, T. W., et al, *Journal of Pharmacology and Experimental Therapeutics*, 229, pages 747 to 755 (1984), rat cerebral cortex tissue is treated with radiolabeled cis-methyldioxalane, a known muscarinic binding site agonist. The concentration of test compound required to inhibit 50% of the binding of this muscarinic agonist is then determined. This procedure allows a determination of the affinity of the test compound for the central muscarinic agonist site. The values for the RQNB and RCMD assay are shown in the table as $IC_{50}$ concentrations.

In the Muscarinic Induced Inositol Phosphate Accumulation Assay (MIPA) human SK-N-SH cells bearing muscarinic binding sites are incubated with the test compound. The production of inositol phosphates is then measured. Stimulation of inositol phosphate turnover reflects the degree of muscarinic agonist activity of the test compound. The concentration of test compound required to produce a response 50% of the maximum is then determined.

| Biological Activity of Compounds of Formula I | | | | | |
|---|---|---|---|---|---|
| Example Number | Compound | RCMD (0.1 μM) | RQNB (1 μM) | Agonist Response $ED_{50}$ | Reversal of SIS Hyperactivity MED (mg/kg) |
| 1 | Methyl[methyl[4-(1-pyrrolidinyl)-2-butynyl]]-carbamate, ethanedioate (1:1) (salt) | 14.3 nM | 2660 nM | 10.0 μM | 10 |
| 1f | Methyl methyl[4-(1-piperidinyl)-2-butynyl]-carbamate, ethanedioate (1:1) (salt) | 1570 nM | 4990 nM | | |
| 1g | Methyl[4-(hexahydro-1H-azepin-1-yl)-2-butynyl]methyl-carbamate, ethanedioate (1:1) (salt) | 958 nM | 1950 nM | | |
| 2 | Methyl[4-(dimethylamino)-2-butynyl]-methyl-carbamate ethanedioate (1:1) (salt) | 63 nM | 46,600 nM | 59.2 μM | |
| 3b | Methyl[4-(ethylmethylamino)-2-butynyl]-methyl-carbamate | 84 nM | 8840 nM | | |

In the Scopolamine Induced Swimming Assay (SIS) the ability of a test compound to reverse the hyperactive swimming behavior of laboratory rats given scopolamine is determined. In the assay, untreated rats generally swim between 20 to 30 meters during a five-minute test period. Rats given scopolamine at doses of 0.1 mg/kg develop a stereotypical swimming hyperactivity with the swimming distance generally increasing 75-125% above baseline values. This increase in swimming hyperactivity can be reversed by the administration of physostigmine or the cholinergic agonist, arecoline. The effect of scopolamine is centrally mediated. Thus, the ability of the test compound to reverse the hyperactive swimming behavior induced by scopolamine is a measure of the central cholinergic activity of the compound. The Minimal Effective Dose (MED) required for a compound to demonstrate reversal of the scopolamine induced hyperactive swimming activity in laboratory rats is shown in the table.

A compound of Formula I

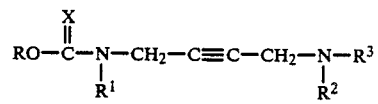

wherein R is
  alkyl of from one to six carbon atoms,
  alkyl of from one to six carbon atoms substituted with hydroxy or alkoxy of from one to four carbon atoms,
  alkenyl of from two to six carbon atoms,
  alkenyl of from two to six carbon atoms substituted with hydroxy or alkoxy of from one to four carbon atoms,
  alkynyl of from two to six carbon atoms,
  alkynyl of from two to six carbon atoms substituted with hydroxy or alkoxy of from one to four carbon atoms,
  cycloalkyl of from three to six carbon atoms,

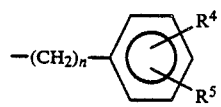

wherein n is zero or an integer of one to eight and $R^4$ and $R^5$ are independently hydrogen, fluorine, chlorine, bromine, hydroxy, alkyl of from one to three carbon atoms, or alkoxy of from one to four carbon atoms, or

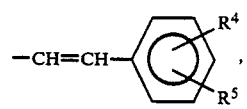

wherein
  $R^4$ and $R^5$ are as defined above;
X is oxygen or sulfur;
$R^1$ is hydrogen,
  alkyl of from one to six carbon atoms,
  alkyl of from one to six carbon atoms substituted with hydroxy or alkoxy of from one to four carbon atoms,
  alkenyl of from three to six carbon atoms,
  alkenyl of from three to six carbon atoms substituted with hydroxy or alkoxy of from one to four carbon atoms,
  alkynyl of from three to six carbon atoms,
  alkynyl of from three to six carbon atoms substituted with hydroxy or alkoxy of from one to four carbon atoms,
  cycloalkyl of from three to six carbon atoms, or

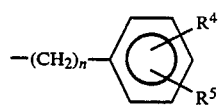

wherein n, $R^4$ and $R^5$ are as defined above:

$R^2$ and $R^3$ are each independently
  hydrogen,
  alkyl of from one to twenty carbon atoms,
  alkyl of from one to twenty carbon atoms substituted with hydroxy or alkoxy of from one to four carbon atoms,
  alkenyl of from three to twenty carbon atoms,
  alkenyl of from three to twenty carbon atoms substituted with hydroxy or alkoxy of from one to four carbon atoms,
  alkynyl of from three to twenty carbon atoms,
  alkynyl of from three to twenty carbon atoms substituted with hydroxy or alkoxy of from one to four carbon atoms,
  cycloalkyl of from three to eight carbon atoms,
  phenyl,
  phenyl substituted with alkyl of from one to four carbon atoms, alkyl of from one to four carbon atoms substituted with hydroxy or alkoxy of from one to four carbon atoms, alkoxy of from one to four carbon atoms, chlorine, bromine, hydroxy, nitro or trifluoromethyl or
$R^2$ and $R^3$ are taken together with the nitrogen atom to which they are attached to form a ring denoted by

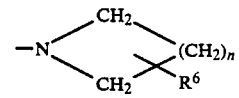

wherein $R^6$ is hydrogen, alkyl of from one to ten carbon atoms, alkyl of from one to ten carbon atoms substituted with hydroxy or alkoxy of from one to four carbon atoms, alkenyl of from two to ten carbon atoms, alkenyl of from two to ten carbon atoms substituted with hydroxy or alkoxy of from one to four carbon atoms, alkynyl of from two to ten carbon atoms or alkynyl of from two to ten carbon atoms substituted with hydroxy or alkoxy of from one to four carbon atoms and n is as defined above,

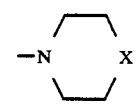

wherein X is as defined above or

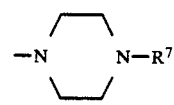

wherein $R^7$ is hydrogen or alkyl of from one to six carbon atoms, or
a pharmaceutically acceptable acid addition salt thereof, may be prepared by reacting a compound of Formula II

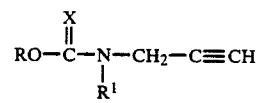

wherein R, $R^1$, and X are as defined above with a compound of Formula III

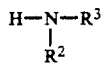

wherein $R^2$ and $R^3$ are as defined above in the presence of paraformaldehyde, a catalyst such as, for example, cuprous chloride and the like and a solvent such as, for example, dioxane and the like at about 25° C. to about the reflux temperature of the solvent to give a compound of Formula I.

Additionally, a compound of Formula I may be prepared by reacting a compound of Formula II and a compound of Formula III in the presence of an aqueous solution of formaldehyde, a catalyst such as, for example, cupric sulfate and the like and adjusting the pH to about 8.5 by the addition of an aqueous solution of a base such as, for example, an aqueous solution of a compound of Formula III at about 25° C. to about 100° C. to give a compound of Formula I.

A compound of Formula II

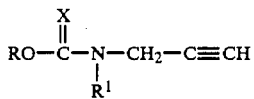

wherein R, $R^1$, and X are as defined above may be prepared by reacting a compound of Formula IV

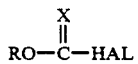

wherein HAL is a halogen atom and R and X are as defined above with a compound of Formula V

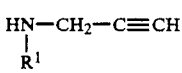

wherein $R^1$ is as defined above in a solvent such as, for example, tetrahydrofuran and the like at about 25° C. to about the reflux temperature of the solvent to give a compound of Formula II.

Alternatively, a compound of Formula 1 may be prepared by reacting a compound of Formula VI

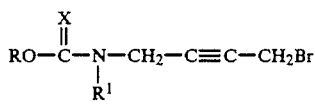

wherein R, $R^1$, and X are as defined above with a compound of Formula III to give a compound of Formula I.

A compound of Formula VI may be prepared by reacting a compound of Formula $I_a$

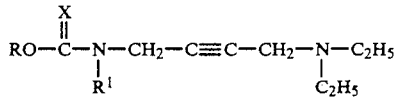

wherein R, $R^1$, and X are as defined above with cyanogen bromide in a solvent such as, for example, diethyl ether and the like at about 25° C. to give a compound of Formula VI.

Compounds of Formula III, Formula IV and Formula V are either known or capable of being prepared by methods known in the art.

The compounds of the present invention can be prepared and administered in a wide variety of oral and parenteral dosage forms. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions.

These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.7 to 7000 mg depending upon the particular application and the potency of the active component. The composition can, if desired, also contain other compatible therapeutic agents.

In therapeutic use as centrally active muscarinic agents the compounds utilized in the pharmaceutical method of this invention are administered at the initial dosage of about 0.01 to about 100 mg per kilogram daily. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting examples illustrate the inventors' preferred methods for preparing the compounds of the invention.

EXAMPLE 1

Methyl[methyl4-(1-pyrrolidinyl)-2-butynyl]]-carbamate, ethanedioate (1:1) (salt)

A solution of methyl N-methyl-N-(2-propynyl) carbamate (3.8 g, 0.03 mol) (Example A), paraformaldehyde (0.9 g, 0.03 mol), pyrrolidine (2.6 g, 0.03 mol), and a spatula tip of cuprous chloride in 150 ml of anhydrous dioxane is allowed to reflux for two hours. After cooling the solution is made strongly acidic with a 2 N solution of hydrochloric acid and washed with diethyl ether. The aqueous solution is then made basic by the addition of solid potassium carbonate until saturated, followed by extraction with diethyl ether (2X). The diethyl ether solution is dried over magnesium sulfate, filtered, and concentrated to afford a yellow oil. The oxalate salt is formed directly from this material; mp 80°-83°C.

In a process analogous to Example 1 using appropriate starting materials the corresponding compounds of Formula I are prepared:

EXAMPLE 1a

Methyl[4-(1-pyrrolidinyl)-2-butynyl]-carbamate, ethanedioate (1:1) (salt); mp 129°-131° C.

EXAMPLE 1b

Methyl ethyl[4-(1-pyrrolidinyl)-2-butynyl]-carbamate; clear amber viscous liquid; Nuclear Magnetic Resonance (NMR)(CDCl$_3$): 4.11 (m, 2H); 4.01 (m 4H); 3.15 (m, 4H); 2.84 (s, 3H); 1.88 (m, 4H); 1.16 (t, J =7.1 Hz, 3H).

EXAMPLE 1c

Ethyl[4-(1-pyrrolidinyl)-2-butynyl]-carbamate ethanedioate (1:1) (salt); mp 90°-94° C.

EXAMPLE 1d

Ethyl methyl[4-(1-pyrrolidinyl)-2-butynyl]-carbamate, ethanedioate (1:1) (salt); mp 68°-70° C.

EXAMPLE 1e

Ethenyl methyl[4-(1-pyrrolidinyl)-2-butynyl]-carbamate, ethanedioate (1:1) (salt); mp 80°-82° C.

EXAMPLE 1f

Methyl methyl[4-(1-piperidinyl]-2-butynyl-carbamate, ethanedioate (1:1) (salt); mp 101°-102° C.

EXAMPLE 1g

Methyl[4-(hexahydro-1H-azepin-1-yl]-2-butynyl]methylcarbamate, ethanedioate (1:1) (salt); mp 98.5°-100° C.

EXAMPLE 1h

Methyl methyl4-(4-methyl-1-piperazinyl]-2-butynyl]-carbamate, dihydrochloride; mp 192°-195° C. (d).

EXAMPLE 1i

Methyl[4-(diethylamino)-2-butynyl]methyl-carbamate, monohydrochloride; mp 88°-90° C.

EXAMPLE 1j

Methyl[4-(3-hydroxypropyl)methylamino]-2-butynyl]-methyl-carbamate; clear gold viscous liquid. NMR(CDCl$_3$): 4.12 (brs, 2H); 3.79 (t, J =5.4 Hz, 2H); 3.73 (s, 3H); 3.39 (t, J =1.9 Hz, 2H); 2.96 (brs, 3H); 2.67 (t, J =5.9 Hz, 2H); 2.33 (brs, 3H); 1.70 (m, 2H).

EXAMPLE 1k

Methyl[4[(4-hydroxybutyl)methylamino-2-butynyl]-methyl-carbamate, ethanedioate (10:13) salt; clear gold viscous liquid. NMR(CDCl$_3$): 4.15 (s, 2H); 4.04 (s, 2H); 3.72 (s, 3H); 3.65 (t, J =5.7 Hz, 2H); 3.23 (m, 2H); 2.96 (s, 3H); 2.88 (s, 3H); 1.61-1.84 (m, 4H).

EXAMPLE 1l

Methyl methyl[4-(4-morpholinyl)-2-butynyl]-carbamate, ethanedioate (1:1) (salt); mp 109°-111° C.

EXAMPLE 2

Methyl[4-(dimethylamino)-2-butynyl]methyl-carbamate, ethanedioate (1:1)(salt)

A solution of 40% aqueous dimethylamine (5.6 ml, 0.05 mol) in water (60 ml) is adjusted to pH 9 by addition of concentrated sulfuric acid. Formaldehyde (4.9 ml, 0.06 mol), methyl N-methyl-N(2-propynyl)carbamate (5.1 g, 0.04 mol) (Example A) and cupric sulfate (0.5 g) is added and the pH adjusted to 8.5 by addition of aqueous dimethylamine. The solution is heated to 100° C. under a dry ice condenser for 2.5 hours. After cooling, the solution is allowed to stir overnight. The solution is filtered through celite and made basic with solid potassium carbonate. The solution is extracted with chloroform (5×300 ml), dried over magnesium sulfate, and concentrated. The resulting oil is purified by bulb to bulb distillation under high vacuum and the ethanedioate salt formed; mp 84°-86° C.

EXAMPLE 3

Methyl[4-(1-azetidinyl]-2-butynyl]methyl-carbamate

A solution of methyl[4-(diethylamino)-2-butynyl]-methyl-carbamate (4.2 g, 0.02 mol) (Example 1i) in anhydrous diethyl ether (50 ml) is added dropwise at room temperature to a stirred solution of cyanogen bromide in anhydrous diethyl ether (40 ml). The mixture is allowed to stand for 12 hours and the diethyl ether layer is separated, washed with water (40 ml), dried over magnesium sulfate, and concentrated. The resulting oil is then purified by bulb to bulb distillation under high vacuum to give methyl N-(4-bromo-2-butynyl)-N-methylcarbamate as a ight yellow oil. Azetidine (2 g, 0.032 mol) is added to a stirred solution of methyl N-(4-bromo-2-butynyl)-N-methylcarbamate (3.6 g, 0.016 mol). The mixture is kept at room temperature for one hour and then filtered. The filtrate is concentrated and the resulting oil purified by bulb to bulb distillation under high vacuum to give a light yellow oil. NMR(CDCl$_3$): 4.10 (brs, 2H); 3.7 (s, 3H); 3.39 (brs, 2H); 2.94 (s, 3H); 2.45 (brs, 4H).

In a process analogous to Example 3 using appropriate starting materials the corresponding compounds of Formula I are prepared:

EXAMPLE 3a

Methyl methyl[4-(methylamino)-2-butynyl]-carbamate; yellow liquid. NMR(CDC$_3$): 4.07 (brs, 2H); 3.68 (s, 3H); 3.36 (t, J = 1.9 Hz, 2H); 2.92 (s, 3H); 2.42 (s, 3H); 1.5 (brs, 1H).

EXAMPLE 3b

Methyl[4-(ethylmethylamino]-2-butynyl]methyl-carbamate; yellow liquid. NMR(CDCl$_3$): 4.06 (brs, 2H); 3.66 (s, 3H); 3.27 (brs, 2H); 2.90 (s, H); 2.29 (t, J =7.2 Hz, 2H); 2.23 (s, 3H); 1.00 (t, J =7.2 Hz, 3H).

EXAMPLE 3c

Methyl methyl[4-[methyl(2-propynyl)amino]-2-butynyl]carbamate; yellow liquid. NMR(CDCl$_3$): 4.12 (brs, 2H); 3.72 (s, 3H); 3.37 (s, 3H); 2.96 (s, 4H); 2.37 (s, 3H); 2.25 (t, J =2.3 Hz, 1H).

PREPARATION OF STARTING MATERIAL

EXAMPLE A

Methyl N-methyl-N-(2-propynyl)carbamate

To a solution of triethylamine (75.8 g, 0.75 mol) and N-methylpropargylamine (50 g, 0.72 mol) in 750 ml of anhydrous tetrahydrofuran is added dropwise methyl chloroformate (68.5 g, 0.72 mol). The solution is allowed to reflux for one hour, cooled, water added, and the aqueous layer extracted with diethyl ether. The diethyl ether solution is dried over magnesium sulfate, filtered, and concentrated to give 78.6 g of a light yellow oil. NMR(CDC$_3$): 4.15 (m, 2H); 3.61 (s, 3H); 2.87 (s, 3H); 2.17 (m, 2H).

We claim:

1. A compound of Formula I

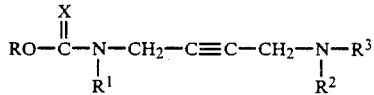

wherein
R is
alkyl of from one to six carbon atoms,
alkyl of from one to six carbon atoms substituted with hydroxy or alkoxy of from one to four carbon atoms,
alkenyl of from two to six carbon atoms,
alkenyl of from two to six carbon atoms substituted with hydroxy or alkoxy of from one to four carbon atoms,
alkynyl of from two to six carbon atoms,
alkynyl of from two to six carbon atoms substituted with hydroxy or alkoxy of from one to four carbon atoms,
cycloalkyl of from three to six carbon atoms,

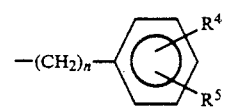

wherein n is zero or an integer of one to eight and $R^4$ and $R^5$ are independently hydrogen, fluorine, chlorine, bromine, hydroxy, alkyl of from one to three carbon atoms, or alkoxy of from one to four carbon atoms, or

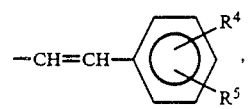

wherein
$R^4$ and $R^5$ are as defined above;
X is oxygen or sulfur;
$R^1$ is
alkyl of from one to six carbon atoms,
alkyl of from one to six carbon atoms substituted with hydroxy or alkoxy of from one to four carbon atoms,
alkenyl of from three to six carbon atoms
alkenyl of from three to six carbon atoms substituted with hydroxy or alkoy of from one to four carbon atoms,
alkynyl of from three to six carbon atoms,
alkynyl of from three to six carbon atoms substituted with hydroxy or alkoxy of from one to four carbon atoms,
cycloalkyl of from three to six carbon atoms, or

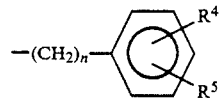

wherein n, $R^4$ and $R^5$ ar as defined above;
$R^2$ and $R^3$ are each independently
hydrogen,
alkyl of from one to twenty carbon atoms,
alkyl of from one to twenty carbon atoms substituted with hydroxy or alkoxy of from one to four carbon atoms,
alkenyl of from three to twenty carbon atoms,
alkenyl of from three to twenty carbon atoms substituted with hydroxy or alkoxy of from one to four carbon atoms, alkynyl of from three to twenty carbon atoms,
alkynyl of from three to twenty carbon atoms substituted with hydroxy or alkoxy of from one to four carbon atoms,
cycloalkyl of from three to eight carbon atoms,
phenyl,
phenyl substituted with alkyl of from one to four carbon atoms, alkyl of from one to four carbon atoms substituted with hydroxy or alkoxy of from one to four carbon atoms, alkoxy of from one to four carbon atoms, chlorine, bromine, hydroxy, nitro or trifluoromethyl or
$R^2$ and $R^3$ are taken together with the nitrogen atom to which they are attached to form a ring denoted by

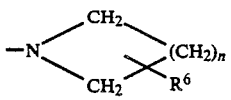

wherein $R^6$ is hydrogen, alkyl of from one to ten carbon atoms, alkyl of from one to ten carbon atoms substituted with hydroxy or alkoxy of from one to four carbon atoms, alkenyl of from two to ten carbon atoms, alkenyl of from two to ten carbon atoms substituted with hydroxy or alkoxy of from one to four carbon atoms, alkynyl of from two to ten carbon atoms or alkynyl of from two to ten carbon atoms substituted with hydroxy or alkoxy of from one to four carbon atoms and n is as defined above,

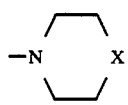

wherein X is as defined above or

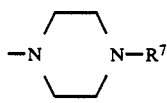

wherein $R^7$ is hydrogen or alkyl of from one to six carbon atoms, or
a pharmaceutically acceptable acid addition salt thereof.

2. A compound according to claim 1, in which
R is
  alkyl of from one to six carbon atoms, or
  alkenyl of from two to six carbon atoms;
X is oxygen;
$R^1$ is alkyl of from two to six carbon atoms;
$R^2$ and $R^3$ are each independently
  hydrogen,
  alkyl of from one to twenty carbon atoms,
  alkyl of from one to twenty carbon atoms substituted with hydroxy or alkoxy of from one to four carbon atoms,
  alkenyl of from three to twenty carbon atoms,
  alkynyl of from three to twenty carbon atoms or
  $R^2$ and $R^3$ are taken together with the nitrogen atom to which they are attached to form a ring denoted by

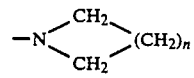

wherein n is zero or an integer from one to eight,

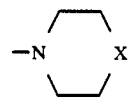

wherein X is oxygen or sulfur or

wherein $R^7$ is hydrogen or alkyl of from one to six carbon atoms.

3. A compound according to claim 2, in which
R is
  methyl, ethyl, or ethenyl;
X is oxygen;
$R^1$ is methyl, or ethyl;
$R^2$ and $R^3$ are each independently hydrogen, methyl, ethyl, $—(CH_2)_n—OH$, wherein n is an intenger from three to four, $—CH_2C\equiv CH$ or $R^2$ and $R^3$ are taken together with the nitrogen atoms to which they are attached to form a ring denoted by

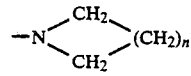

wherein n is zero or an integer from one to six,

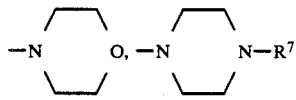

wherein $R^7$ is hydrogen or methyl.

4. A compound according to claim 3, selected from the group consisting of:
methyl[methyl[4-(1-pyrrolidinyl)-2-butynyl]]carbamate;
methyl methyl[4-(1-piperidinyl)-2-butynyl]carbamate;
methyl[4-(hexahydro-1H-azepin-1-yl)-2-butynyl]methyl-carbamate;
methyl[4-(dimethylamino)-2-butynyl]methylcarbamate;
methyl[4-(ethylmethylamino)-2-butynyl]methyl-carbamate;
methyl ethyl[4-(1-pyrrolidinyl)-2-butynyl]carbamate;
ethyl methyl[4-(1-pyrrolidinyl)-2-butynyl)]carbamate;
ethenyl methyl[4-(1-pyrrolidinyl)-2-butynyl)]carbamate;
methyl[4-(1-azetidinyl)-2-butynyl]methyl-carbamate;
methyl methyl[4-(4-morpholinyl)-2-butynyl]carbamate;
methyl methyl[4-(4-methyl-1-piperazinyl) 2-butynyl]-carbamate;
methyl methyl[4-(methylamino)-2-butynyl]carbamate;
methyl[4-(diethylamino)-2-butynyl]methylcarbamate;
methyl methyl [4-methyl(2-propynyl)amino]2-butynyl]-carbamate;

methyl[4-[(3-hydroxypropyl)methylamino]2-butynyl]-methyl-carbamate; and methyl[4-[(4-hydroxybutyl)methylamino]2-butynyl]-methyl-carbamate.

5. A method of treating the symptoms of cognitive decline in an elderly patient comprising a cholinergically effective amount of a compound according to claim 1.

6. A pharmaceutical composition for the treatment of the symptoms of cognitive decline in an elderly patient comprising a cholinergically effective amount of a compound according to claim 5 in combination with a pharmaceutically acceptable carrier.

* * * * *

UNITED STATES PATENT AND TRADEMARK OFFICE
CERTIFICATE OF CORRECTION

PATENT NO. : 4,996,201
DATED : February 26, 1991
INVENTOR(S) : S. C. Bergmeier, et al It is certified that error appears in the above—identified patent and that said Letters Patent is hereby corrected as shown below:

In column 16, line 44,
    delete "alkoy" and insert --alkoxy--.
In column 16, line 58,
    delete "ar" and insert --are--.

Signed and Sealed this

Twenty-first Day of July, 1992

Attest:

DOUGLAS B. COMER

Attesting Officer        Acting Commissioner of Patents and Trademarks